(12) United States Patent
Mueller et al.

(10) Patent No.: US 7,895,881 B2
(45) Date of Patent: Mar. 1, 2011

(54) APPARATUS FOR DETECTION OF CHEMICAL OR BIOLOGICAL SUBSTANCES AND METHOD FOR CLEANING THE APPARATUS

(75) Inventors: Gerhard Mueller, Grafing (DE); Andreas Helwig, Munich (DE); Johann Goebel, Munich (DE)

(73) Assignee: EADS Deutschland GmbH, Ottobrunn (DE)

( * ) Notice: Subject to any disclaimer, the term of this patent is extended or adjusted under 35 U.S.C. 154(b) by 611 days.

(21) Appl. No.: 11/874,672

(22) Filed: Oct. 18, 2007

(65) Prior Publication Data

US 2009/0101165 A1    Apr. 23, 2009

(51) Int. Cl.
   *G01N 21/80* (2006.01)
(52) U.S. Cl. .................... 73/31.03; 73/23.34; 73/31.01; 73/31.02; 73/31.05
(58) Field of Classification Search .................. 73/23.2, 73/23.3–23.34, 31.01–31.07
   See application file for complete search history.

(56) References Cited

U.S. PATENT DOCUMENTS

| | | | |
|---|---|---|---|
| 5,656,827 A * | 8/1997 | Kang et al. | 257/76 |
| 7,579,052 B2 * | 8/2009 | Boiadjiev et al. | 427/595 |
| 2006/0231420 A1 * | 10/2006 | Garzon et al. | 205/775 |

OTHER PUBLICATIONS

Helwig et al., "Gas sensing interactions at hydrogenated diamond surfaces", IEEE Sensors Journal, vol. 7, No. 9, pp. 1349-1353, Sep. 2007.*

Rezek et al., "Intrinsic hydrogen-terminated diamond as ion-sensitive field effect transistor", Sensors and Actuators B, vol. 122, No. 2, 17, pp. 596-599, Aug. 2006.*

Gi et al., "Possibility of realizing a gas sensor using surface conductive layer on diamond films" Japanese Journal of Applied Physics, Japan Society of Applied Physics, Tokyo, JP, vol. 36, No. 4A, pp. 2057-2060, Apr. 1999.*

Tanielian et al., "Effect of adsorbates and insulating layers on the conductance of plasma deposited a-Si:H", Journal of Non-Crystalline Solids, vol. 35-36, pp. 575-580, Jan. 1980.*

Ferreira et al., "Porous a/nc-Si:H films produced by HW-CVD as ethanol vapour detector and primary fuel cell", Sensors and Actuators B 103, pp. 344-349, May 2004.*

Mariucci et al., "Hydrogenated amorphous silicon technology for chemically sensitive thin-film transistors", Sensors and Actuators B, vol. 6 pp. 29-33, 1992.*

Mueller et al., "Hydrogen incorporation, doping and thickness dependent conductivity in glow discharge deposit a -Si:H Films", Journal of Non-Crystalline Solids 59 & 60, pp. 469-472, 1983.*

Gi et ali., "Hall Effect Measurements of Surface Conductive Layer on Undoped Diamond Films in NO2 and HH3 Atmospheres", Jpn. J. Appl Phys. vol. 37, No. 6A, pp. 3492-3496, Jun. 1999.*

Garrido et al., "pH Sensors Based on Hydrogenated Diamon Surfaces", Applied Physics Letters, vol. 86, Mar. 2005.*

* cited by examiner

*Primary Examiner*—David A. Rogers
(74) *Attorney, Agent, or Firm*—Crowell & Moring LLP

(57) ABSTRACT

A device for detecting chemical or biological substances includes an analytical instrument for detecting the substances and for providing information concerning the qualitative or quantitative presence of the substances, and also a contamination sensor for measuring the degree of contamination of the analytical instrument and/or of the device.

11 Claims, 1 Drawing Sheet

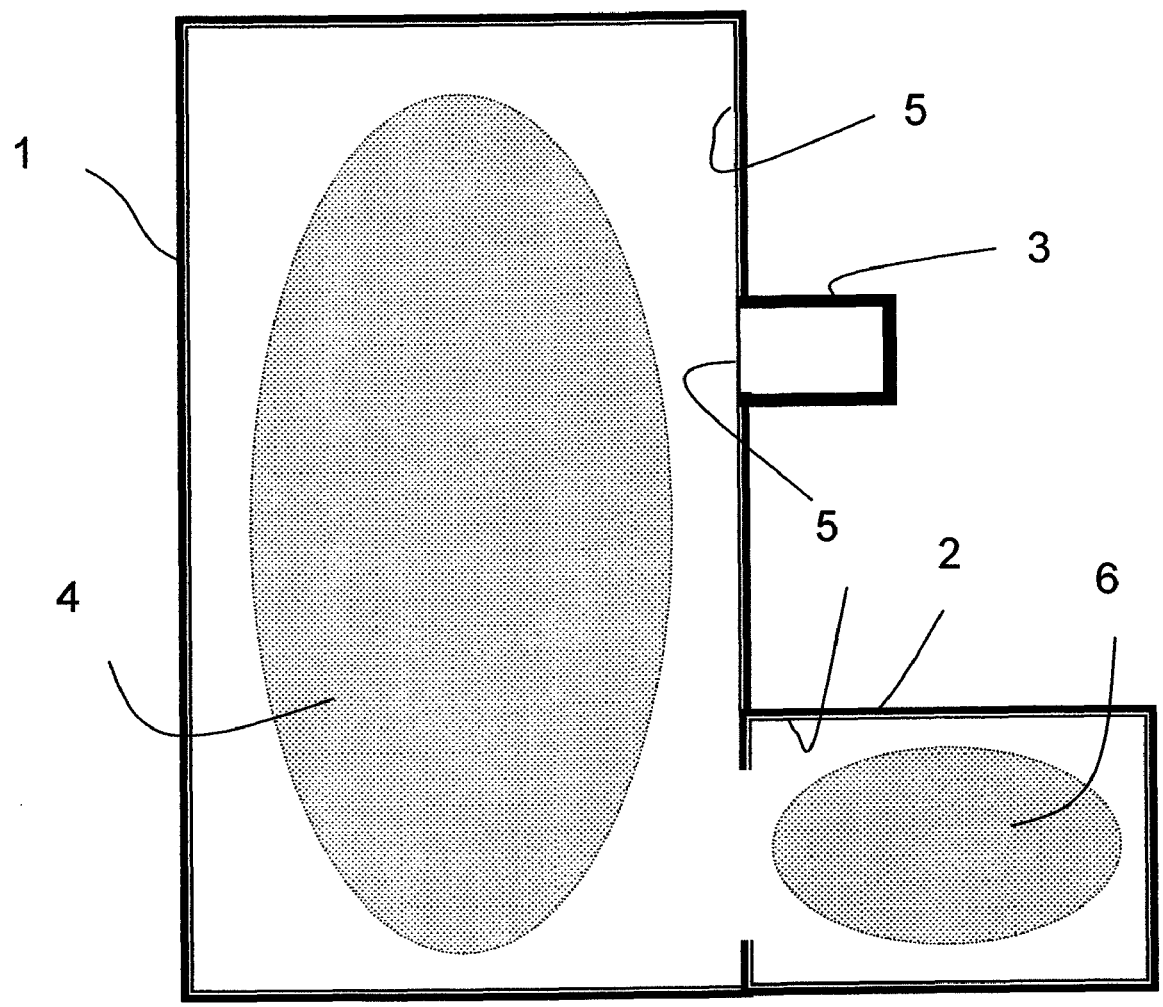
Figure

APPARATUS FOR DETECTION OF CHEMICAL OR BIOLOGICAL SUBSTANCES AND METHOD FOR CLEANING THE APPARATUS

BACKGROUND AND SUMMARY OF THE INVENTION

The invention relates to a device for detecting chemical or biological substances, having an analytical instrument for detecting the substances and for providing information concerning the qualitative or quantitative presence of the substances. Furthermore, the invention also relates to a method of cleaning the device and the analytical instrument contained therein.

Such detection devices are used for security screening portals (SSP) which are frequently found at airports, at secured passage ways of buildings and the like. The devices are used principally to detect chemical or biological substances, and in particular to avoid terror attacks by explosives. In such portals, a person or an object is exposed to one or more air blasts in order to detach any explosive particles that may be present on the clothing or the surface, and to deliver the latter to the detector usually constructed as an ion mobility spectrometer (IMS). At the site of the detector, these are then converted to gaseous fragments—particularly nitrogen oxides (NOx)—, by which the explosive can be identified.

In practical operation, the above-mentioned systems have a high false alarm rate, which leads to problems because of the resulting delays, particularly in the processing of passengers. During the operation of such devices, the detectors are exposed to many different smelling substances, which have a tendency to accumulate on the interior surfaces of such portals, where they may be converted to secondary substances, and can prevent a reliable detection of traces of explosives in the most unfavorable case.

By means of measurements, it can be shown that thin water layers may be created by adsorption of ambient humidity on the interior surfaces of the portals, as well as by adsorption within the analytical instruments themselves. Such water layers, in turn, can relatively rapidly absorb and accumulate electrolytically dissociating vapors which subsequently are very slowly emitted again into the environment. In this desorption process, particularly a background of gaseous $NO_2$ and/or of solid ammonium nitrate may form in the analytical instrument. Both trace substances can negatively influence the ability of detecting explosives.

It is therefore an object of the present invention to provide an improved device for the detection of chemical or biological substances, such that distortions of the detector for the detection of chemical of biological substances are reduced or avoided.

This and other objects and advantages are achieved by the method and apparatus according to the invention in which the detection device includes, in addition to the detection instrument, a contamination sensor that is constructed for measuring the degree of a contamination of the detector and/or of the device. More particularly, the invention is based on the idea of providing a sensor inside the device which measures the degree of contamination of the surfaces as well as particularly that of the analytical instrument. As a result, this contamination sensor provides a signal by which a need for cleaning the device (and particularly of the analytical instrument) can be determined. False alarms can thereby be reduced and an optimum cleaning interval can be determined, so that the cleaning will only take place when it is required. In addition, there is no further distortion of the measuring results, so that the sensor can also be reused after the cleaning. Contaminations in the analytical instrument by adsorption of water-soluble gases on the housing of the device or of the portal can be detected early. A required cleaning of the analytical instrument is therefore indicated early.

According to one aspect of the invention, the contamination condition of adsorbed water layers within the device and the analytical instrument respectively is detected by means of a contamination sensor and resulting problems during the interpretation of the analytical results are indicated.

According to another aspect of the invention, cleaning processes at the interior surfaces of the device and of the analytical instrument respectively, are initiated as soon as the output signal of the contamination sensor exceeds a threshold value.

Hereinafter, the function of a contamination sensor according to the invention, arranged inside a device for the detection of chemical or biological substances, will be described in detail. A sensor of this type consists, for example, of a diamond crystal having a hydrogenated surface.

In principle, undoped diamond crystals are nonconductors. It has been found, however, that undoped diamonds having hydrogenated surfaces have a P-type surface conductivity which depends on the presence of a thin adsorbed water layer. The thickness of this layer is estimated to be approximately 1 nm. It is found that the amount of surface conductivity is a function of the pH value in the adsorbed water layer. The latter, in turn, is influenced by the presence of electrolytically dissociating gases or vapors in the ambient gaseous atmosphere. Since air moisture can in principle adsorb on any surface, it is found that the processes of a dissociation into the moisture layer can take place on any surface, including in particular the surfaces of the security screening portal and likewise in the interior of the analytical instruments and measuring devices; without, however, causing simultaneously measurable effects.

The storage capacity of absorbed water coatings could be detected by exposing an HD (hydrogenated diamond) sensor to different acid and base vapors. In this case, a reaction of the sensor takes place upon two successive exposures to $HNO_3$ vapors and $NH_4OH$ vapors. In the former case, $NO_2$ vapors (that is, reactive gases) develop over the acid, which are present everywhere in variable concentrations in the form of combustion gases. $NH_3$ vapors develop in the latter case. $NH_3$ may occur in the ambient air as a result of agricultural emissions. Furthermore, $NH_3$ is chemically related to the large group of amines present in many smelling substances.

In this case, it is found that acid-containing and base-containing vapors have a strong and opposite reaction to the electric conductivity of an HD sensor. It is also been found that the absorption of these vaporous contaminations in the adsorbed moisture layer takes place very rapidly. In this case, the recovery of the sensor signal takes place very slowly, which can be recognized by a signal drop by approaching the neutral point (pH=7).

The slow decay after a concluded exposure can be explained by the hydration of the $NO_3$— ions that follows in the dissolution process (hydration=formation of a coordination sphere of aligned water dipoles around the central $NO_3$— ion). This hydration makes the re-evaporation of the absorbed $NO_2$ more difficult. In connection with the portal surfaces, this means that $NO_2$ present in the environment in low concentrations accumulates in the moisture layers absorbed on the walls and, in the future, may be released again over long periods of time. Similar considerations therefore also apply to the case of an $NH_3$ exposure. In particular, the absorption of the $NH_3$ again takes place quite rapidly and, in contrast, the release occurs very slowly. The fact that the sensor resistance again approaches the sensor base resistance after the $NH_3$ exposure suggests a neutralization effect.

Further investigations with other substances show that reactions may occur that have different intensities as a function of the substances. On the whole, examinations showed that particularly strong reactions are to be expected in the case of the $NO_2$ overlying the detection of explosives and in the case of the amine-type smelling substances. Reactions of different intensities can be explained by the variability of three quantities which concern the vapor pressure of the various liquids, the solubility of the vapors in the liquid electrolyte on the sensor surface and the ease by which an electrolytic dissociation can take place in the absorbed water layer. In the following, Table 1 shows the vapor pressure, the solubility and the dissociation capacity of different vapors in water.

TABLE 1

Vapor Pressure, Solubility and Dissociation Capacity of Various Vapors in Water

| Acid/Base | $P_{vapor}$ (20° C.) | Solubility | $pK_a/pK_b$ |
|---|---|---|---|
| HCL | 4260 mbar | Good Solubility in in water (850 g/L) | −6 |
| $HNO_3$ | 9.4 mbar (68%) 56 mbar (100%) | Completely mixable with water | −1.32 |
| $H_2SO_4$ | 0.0001 mbar | Completely mixable with water | −3 |
| $H_3PO_4$ | 0.038 mbar | Completely mixable With water | 1.96 |
| $CH_2O_2$ | 28 mbar | Mixable with water ethanol and glycol | 3.75 |
| $NH_3$ | 8.572 bar | Mixable with water (702 liters of $NH_3$ in 1 liter of $H_2O$) | $pKa = 23$, $pKb = -9$ |
| NaOH | 1.19 mbar | Well mixable with Water | |
| $H_2O_2$ | 1.9 mbar | Completely mixable with water | 11.6 |
| $(CH_3)_2CO$ (acetone) | 233 mbar | Well mixable with water | 20 |

The sensor preferably has a semiconductor surface with a moisture film, the pH value of the moisture film being measurable and the substances being dissociable into the moisture film. The pH value of the moisture film can be changed by the dissociation, in which case a charge transfer is generated into the semiconductor, so that the sensor is constructed as a pH sensor and is used as a threshold value sensor. The device has a transducer which is constructed for measuring the charge transfer in the semiconductor. Such transducers are also called converters which, independently of the physical quantity of a received signal, provide an electric voltage, which are in a known or determinable connection with the measured quantity, so that the signal can be further processed. In the present case, the converter is constructed to permit the measurement of the charge transfer into the semiconductor, so that the change of the charge transfer is measured by the converter (transducer). The contamination of the measuring device or of the portal can therefore be read off the sensor or off a connected read-out device.

The detector and/or the sensor according to the invention is advantageously constructed as an HD sensor, and has a diamond crystal with a hydrogenated surface having a surface conductivity. The device may be constructed, for example, as a component of a security gate or of a portal for the detection of substances on persons and/or objects. In particular, such devices are suitable for equipping security gates on airports or security-relevant buildings in order to check persons with respect to chemical or biological substances.

The present invention also provides a method of cleaning a chemical or biological substances detection device and the analytical instrument contained therein. According to the invention, the point in time when it becomes necessary to clean the device (and the analytical instrument contained therein) is detected by measuring by means of the contamination sensor, and is provided as information. The measuring detection of the point in time takes place by means of a pH value change. When the contamination of the analytical instrument or of the device reaches a value at which cleaning is required, the point in time of the cleaning as well as the span of the cleaning interval may be proportioned by means of information provided by the contamination sensor. The occurrence of false alarms can thereby be excluded because, when the method according to the invention is used, the degree of contamination at which a false alarm can be triggered will no longer be reached. In the following, several methods are therefore described for the cleaning of surfaces for the reduction and prevention of interfering substances on the analytical instruments as well as on the portal or the device.

One cleaning method utilizes a thermal evaporation of the surface water, which may also be a thermally accelerated, driving dissolved substances out of the absorbed water layer. It is known that the surface water quantitatively evaporates at temperatures of approximately 200° C. A temperature of 150° C., preferably a temperature of 175° C. and particularly preferably a temperature of approximately 200° of the sensor or the detector is therefore provided in order to cause reliable evaporation of the water layer on the respective surface.

Another method for cleaning the corresponding surfaces is implemented by using oxidants, such as electrically generated ozone or metered added hydrogen peroxide ($H_2O_2$), upon the surfaces. For example, the resistance of the hydrogenated diamond can be reduced by means of a multiple action of ozone with a fraction of 300 ppb back to a neutral value.

Another method of cleaning the sensor surfaces includes irradiation of the semiconductor surface provided with the moisture film, using ultraviolet light. In this case, photocatalytical effects can be generated which lead to an accelerated reduction of the adsorbed chemical contaminations.

A photocatalytical cleaning of the interior surfaces of the device and of the analytical instrument respectively can be achieved by the application of nanocrystalline powder of titanium oxide.

The necessity of the above-described cleaning method can be demonstrated within the scope of the present invention by the following experiment: After a dissociation of $HNO_3$ and $NH_3$ exposures, which were carried out successively, a fast return to the sensor base line was observed. This compensation effect can be reached by the formation and precipitation of a saline compound according to

NO3-+NH4+→ammonium nitrate.

However, ammonium nitrate itself is an explosive. The collection and detection of precipitated particles can therefore easily lead to false alarms. In order to prevent the generation of direct interfering substances, the absorption layers in a security screening portal should be photo-catalytically cleaned after each measurable deviation from the neutral point of the sensor base line (pH=7). In the latter case, a true cleaning according to the reaction equation

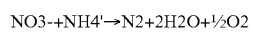
NO3-+NH4'→N2+2H2O+½O2 can be used as the basis. As a result of the above-mentioned methods for cleaning the detector surfaces and for the reduction and prevention of interfering substances on the surfaces, an automatic cleaning system can be developed, so that at least one of the above-mentioned cleaning methods can be used for cleaning the sensor surfaces when the sensor for the detection of the contamination provides the information for the cleaning.

Other objects, advantages and novel features of the present invention will become apparent from the following detailed description of the invention when considered in conjunction with the accompanying drawings.

BRIEF DESCRIPTION OF THE DRAWINGS

The single FIGURE is a schematic view of an embodiment of the present invention.

DETAILED DESCRIPTION OF THE INVENTION

The FIGURE shows a device 1 for the detection of chemical or biological substances that is constructed essentially as rectangular portal. The described preferred embodiment is also called a "security screening portal (SSP)" or security gate, and is used for the detection of chemical or biological substances on persons and/or objects.

The detection of such substances takes place by an analytical instrument 2 which, in the present case, is provided in the form of an ion mobility spectrometer (IMS), and is illustrated as a rectangular box at the right lower edge of the device 1.

In addition, a contamination sensor 3 is provided on the device 1 which, in the FIGURE, is arranged slightly above the analytical instrument 2 laterally on the device 1. In the present embodiment, the contamination sensor 3 is an HD sensor with a diamond crystal having a hydrogenated surface with a surface conductivity. In this case, the sensor surface points to the interior surface of the device 1. The semiconductor surface of the contamination sensor 3 has a moisture film 5 whose pH value can be measured by the contamination sensor 3.

As soon as the contamination sensor 3 detects that the water coatings or moisture films 5 occurring naturally on the interior surfaces of the device 1 and of the analytical instrument 2, contain substances which may impair the function of the analytical instrument, the contamination sensor 3 triggers a cleaning mechanism 4 in the device 1, which is outlined as fog or radiation, and/or a cleaning mechanism 6 in the analytical instrument 2. After the successful cleaning, the device 1 and the analytical instrument 2 are returned to their initial condition and can then again be fully utilized for detecting harmful substances.

In the present embodiment, the cleaning mechanism 4 in the device 1 and the cleaning mechanism 6 in the analytical instrument 2 contain, among other things, a photo catalysis by applying nanocrystalline powder of titanium oxide ($T_iO_2$) to the interior surfaces of the device 1 for the detection of chemical or biological substances and of the analytical instrument 2. Furthermore, a treatment with electrically generated ozone is provided which causes an oxidative conversion of interfering substances. Also, a metered addition of $H_2O_2$ is provided which causes an oxidative conversion of interfering substances.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

The invention claimed is:

1. A device for detecting chemical or biological substances, said device comprising:
    an analytical instrument, having a least one sensor, for detecting the substances and for providing information concerning qualitative or quantitative presence of the substances;
    a contamination sensor providing a contamination signal;
    a processor that determines a degree of contamination of the analytical instrument or the device based at least in part on the contamination signal; and
    a cleaning mechanism coupled to the contamination sensor.

2. The device according to claim 1, wherein:
    the contamination sensor has a semiconductor surface having a moisture film;
    a pH value of the moisture film is measurable; and
    the substances are dissociable into the moisture film.

3. The device according to claim 1, wherein the device comprises a security gate for detection of substances on persons and/or objects.

4. The device according to claim 1, wherein the analytical instrument is an ion mobility spectrometer (IMS) and the contamination sensor has a semiconductor surface having a moisture film, a pH value of the moisture film is measurable, the substances are dissociable into the moisture film, the pH value of the moisture film is changed by the dissociation and a charge transfer into the semiconductor is generated, such that the contamination sensor forms a pH sensor that operates as a threshold value sensor.

5. The device according to claim 1, wherein the contamination sensor includes a semiconductor surface having a moisture film, a transducer that measures a charge transferred from the film to the semiconductor surface, and a converter that measures a change in the charge transferred into the semiconductor.

6. The device according to claim 1, wherein device includes a portal with a first opening for the analytical instrument and a second opening for the contamination sensor, and the cleaning mechanism includes a first cleaning mechanism that cleans the portal and a second cleaning mechanism that cleans the analytical instrument.

7. The device according to claim 1, wherein the contamination sensor is hydrogenated diamond (HD) sensor.

8. The device according to claim 7, wherein the contamination sensor has a diamond crystal, with a hydrogenated surface having a surface conductivity.

9. A device for detecting chemical or biological substances, said device comprising:
    an analytical instrument, having a least one sensor, for detecting the substances and for providing information concerning qualitative or quantitative presence of the substances; and
    a contamination sensor providing a contamination signal;
    a processor that determines a degree of contamination of the analytical instrument or the device based at least in part on the contamination signal, wherein:
    the contamination sensor has a semiconductor surface having a moisture film;
    a pH value of the moisture film is measurable;
    the substances are dissociable into the moisture film,
    the pH value of the moisture film is changed by the dissociation; and a charge transfer into the semiconductor is generated, such that the contamination sensor forms a pH sensor that operates as a threshold value sensor.

10. The device according to claim 9, further comprising a transducer which measures the charge transfer into the semiconductor.

11. A method for detecting chemical or biological substances, said method comprising:

detecting, by an analytical instrument having at least one sensor, the substances;

providing information concerning qualitative or quantitative presence of the substances;

measuring, by a contamination sensor, a pH level on a moisture film of the contamination sensor; and determining, by a processor, a degree of contamination of the analytical instrument or the device based at least in part on the pH level of the moisture film of the contamination sensor.

* * * * *